(12) United States Patent
Llorin et al.

(10) Patent No.: US 6,939,696 B1
(45) Date of Patent: Sep. 6, 2005

(54) CELL DISRUPTION METHOD USING SONICATION

(75) Inventors: Oscar J. Llorin, Catonsville, MD (US); Matthew P. Collis, Seven Valleys, PA (US); Michael C. Little, Baltimore, MD (US); James M. Harris, Columbia, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 666 days.

(21) Appl. No.: 09/128,340

(22) Filed: Aug. 3, 1998

(51) Int. Cl.[7] .................. C12N 1/06; C12N 1/12; C12N 1/16; C12N 1/18; C12N 13/00

(52) U.S. Cl. ................. 435/173.1; 435/173.7; 435/253.1; 435/254.1; 435/255.1; 435/259

(58) Field of Search ............... 435/173.1, 173.7, 435/253.1, 254.1, 255.1, 259, 174, 243, 252.1, 822

(56) References Cited

U.S. PATENT DOCUMENTS

| | | | |
|---|---|---|---|
| 3,558,066 A | | 1/1971 | Alliger |
| 3,771,354 A | * | 11/1973 | Miller ........................ 73/67.7 |
| 3,887,431 A | * | 6/1975 | Robbins et al. ................ 195/5 |
| 4,303,752 A | * | 12/1981 | Kolehmainen et al. ......... 435/8 |
| 5,374,522 A | * | 12/1994 | Murphy et al. ................ 435/6 |
| 5,376,527 A | | 12/1994 | Robson et al. |
| 5,693,500 A | * | 12/1997 | Wood et al. ................ 435/69.3 |
| 5,871,994 A | * | 2/1999 | Kubota et al. ............... 435/200 |
| 5,962,279 A | * | 10/1999 | Nanba et al. ................ 435/106 |
| 6,383,769 B1 | * | 5/2002 | Tsusaki et al. ................ 435/15 |

OTHER PUBLICATIONS

Chang, "Physical Chem with Applications to Biological systems", Second Ed., p. 81, 1977.*
Buck, George E. et al., J. Clin. Microbio.; 30 pp 1331–1334 (May 1992).
De Wit, D. et al., J. Clin. Micro 28 (11):2437–2441 (1990).
Hurley, S.S. et al., J. Clin. Microbiol. 25 (11):2227–2229 (1987).
Shah, J.S. et al., J. Clin. Microbiol. 33 (2):322–328 (1995).
Hurley, S.S. et al., J. Systemic Bacteriology 38 (2):143–146 (1988).
Seiter, J.A. and Jay, J.M., Int. J. Syst. Bacteriol. 30:460–465 (Apr., 1980).
Salter, D.N. and Smith, R.H., British Journal of Nutrition 51:531–539 (1984).
Closs, O et al. Scand. J. Immunol. 12:249–263 (1980).

* cited by examiner

*Primary Examiner*—David M. Nafe
*Assistant Examiner*—Deborah K. Ware
(74) *Attorney, Agent, or Firm*—Allan M. Kiang

(57) ABSTRACT

The present invention relates to a method for disrupting cells by subjecting the cells to ultrasonic energy in the absence of beads. The present invention also relates to the enhancement of cell disruption methods using ultrasonic energy by reducing the surface tension of the liquid in which the cells are located.

7 Claims, 1 Drawing Sheet

CELL DISRUPTION METHOD USING SONICATION

BACKGROUND OF THE INVENTION

Access to cellular components such as nucleic acids is imperative to a variety of molecular biology methodologies. Such methodologies include nucleic acid sequencing, direct detection of particular nucleic acid sequences by nucleic acid hybridization and nucleic acid sequence amplification techniques.

Although access to nucleic acids from the cells of some organisms does not involve particularly complex methodologies or harsh treatments, other organisms have cells from which it is particularly difficult to access nucleic acids or other cellular components. Organisms in the latter group include species of the genus *Mycobacteria,* yeast and fungi. Usually, the difficulty in cellular component access is a result of organism cell walls which are highly resistant to lysis or disruption, and/or the adherence of certain cellular components such as nucleic acids to cellular proteins and other cellular substances such as pieces of cell walls.

Due to the difficulties in attempting to access nucleic acids from mycobacterial organisms the methods utilized tend to be harsh and thus not very useful with non-mycobacterial organisms. Conversely, the methods used to disrupt cells and access nucleic acids from non-mycobacterial organisms are often not effective when used with mycobacterial organisms.

Two non-enzymatic methods which have been used to disrupt cells to access nucleic acids are the application of heat to cells (see U.S. Pat. No. 5,376,527) and physical agitation of cells in the presence of lysogenic chemicals with or without "minibeads". For example, DeWitt et al., *J. Clin. Micro.* 28 (11):2437–2441 (1990) describe the orbital shaking of samples containing mycobacterial cells in the presence of buffered phenol and sodium dodecyl sulfate (SDS), Hurley, S. S. et al, *J. Clin. Microbiol.* 25 (11) 2227–2229 (1987) describe a combination of phenol extraction and physical rupture of mycobacterial cells with zirconium beads in a Biospec Products Mini-Beadbeater, and Shal, J. S. et al. *J. Clin. Microbiol.* 33 (2), 322–328 (1995) describe the lysis of heat-inactivated mycobacterial cells with the lysogenic agent guanidimium thiocyanate (GuSCN) and physical agitation with zirconium oxide beads. Also, U.S. Pat. No. 5,374,522 describes methods of disrupting cells by applying ultrasonic energy to the cells in the presence of beads, and Hurley et al., *Int. J. Systemic Bacteriology* 38 (2):143–146 (1988) describe physical agitation of samples containing mycobacterial cells in the presence of distilled phenol and zirconium beads.

Alternatively, a solution containing mycobacterial microorganisms can be subjected to very intense ultrasonic bombardment in the presence of beads or particles which results in cell breakage. Typically, ultrasonic devices such as powerful ultrasonic probes (known as sonifiers or sonicators) are used in these processes. (See for example, Seiter, J. A. and Jay, J.M., "Application of Polyacrylamide Gel Electrophoresis to the Characterization and Identification of Arthrobacter Species," *Int. J Syst. Bacteriol.,* 30:460–465 (April, 1980)). However, significant amounts of heat are generated with high-powered probe devices of this type, and thus, cooling jackets or ice baths are required to reduce temperatures which can and often damage cellular nucleic acid. This damage to cellular nucleic acid from the high temperatures generated by use of sonicators with beads or particles has been shown by other researchers such as Salter, D. N. and Smith, R. H., "Protein Utilization in the Young Steer: Digestion and Nitrogen Retention of $^{15}$N-Labelled Rumen Bacterial Protein", *British Journal of Nutrition,* 51:531–539 (1984). These types of sonicating devices have measured outputs as high as 80–100 W as taught by Closs, O., et al., "The Antigens of *Mycobacterium bovis,* Strain BCG, Studied by Crossed Immunoelectrophoresis: A Reference System", *Scand. J Immunol.,* 12:249–263 (1980) and Allegro, H., U.S. Pat. No. 3,558,066 entitled "Ultrasonic Extraction of Viable Antigens From Gram-Positive Bacteria," issued Jan. 26, 1971.

In contrast, U.S. Pat. No. 5,374,522 teaches use of a sonicating device which operates at lower power densities. Thus, there is no need for cooling jackets or ice-baths since the units lack the power to raise the temperature of the sonicating suspension to damaging levels. However, the method taught in this patent still requires the presence of beads or particles for effective cell lysis.

As recognized in U.S. Pat. No. 5,374,522, rigorous physical grinding or shaking of organisms whether with or without beads presents considerable drawbacks. First, friction resulting from the physical interaction of grinding particles can create excessive heat which has deleterious effects on nucleic acids, and thus can render the nucleic acids unusable in subsequent hybridization procedures. Also, many of the organisms whose cells require such harsh conditions for extraction of cellular components are extremely pathogenic, and thus present health hazards when subjected to these physical manipulations in an open system. Also, the use of lysogenic chemical agents and/or enzymes such as SDS, GuSCN, proteinases, phenol/chloroform, etc. often adversely affects subsequent molecular biology processes for which the nucleic acids are accessed. For example, ionic and non-ionic detergents are known to inhibit nucleic acid amplification processes such as polymerase chain reaction (PCR) and strand displacement amplification (SDA), and carbon black which is commonly used to process glass beads is known to inhibit SDA.

SUMMARY OF THE INVENTION

The present invention provides an unexpectedly uncomplicated method for lysing cells to access nucleic acids therein. The present invention is a method for lysing cells wherein a sample containing cells is subjected to ultrasonic energy without the presence of beads. Following such lysis, nucleic acid from the cells is available for use in various molecular biology procedures.

BRIEF DESCRIPTION OF THE DRAWINGS

The various objects, advantages and novel features of the invention will be more readily appreciated from the following detailed description when read in conjunction with the appended figures in which.

DETAILED DESCRIPTION OF THE INVENTION

Figure 1:
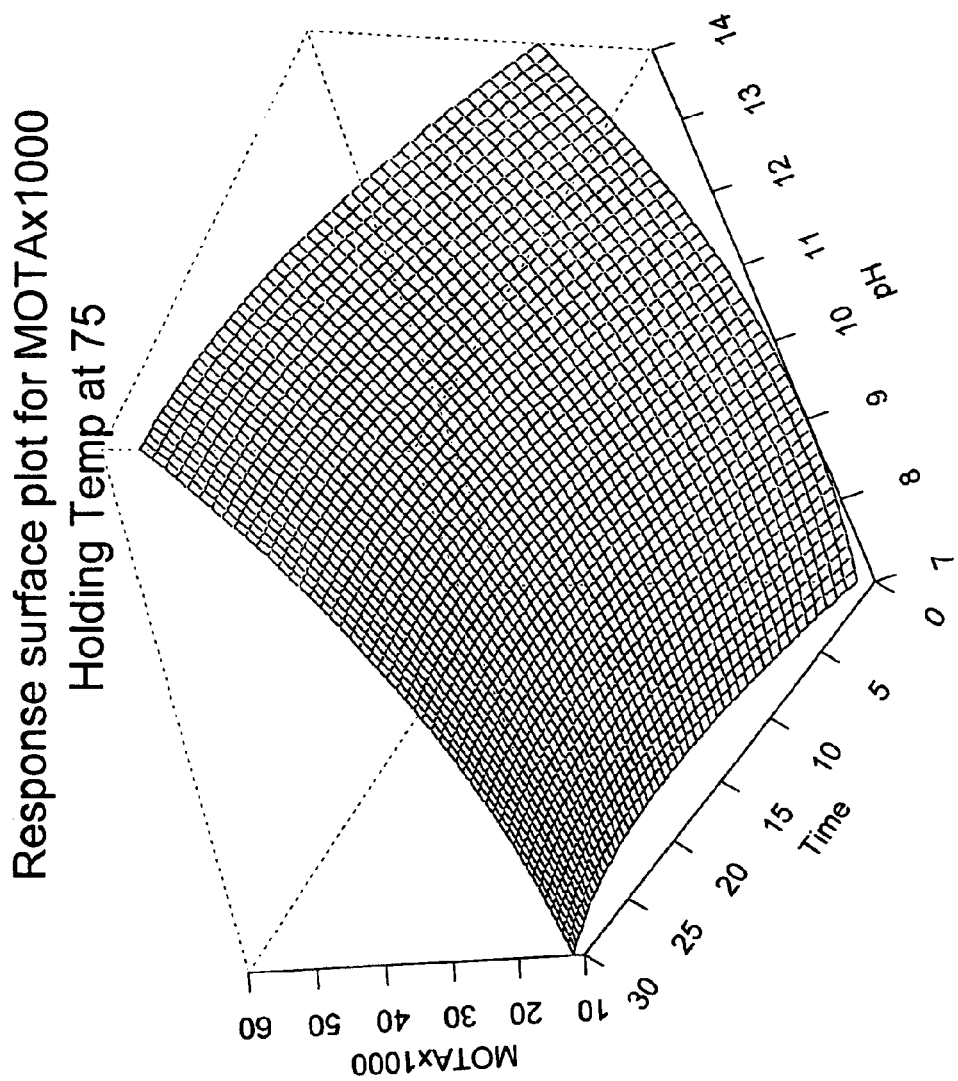
FIG. 1 is a graphical response surface plot showing the results of experiments to optimize the conditions of the method described herein.

In a broad aspect, the method of the present invention provides a simple procedure for disrupting cells in order to access to cellular components including nucleic acids in a form useful for subsequent molecular biology procedures. The method's simplicity results from the limited manipulation of a sample and minimal additions to the sample.

The minimal additions to the sample results from the unexpected discovery that cells, including cells which are notoriously difficult to disrupt, such as mycobacterial cells, are disrupted by the application of ultrasonic energy in the absence of beads. Based on teachings such as those in U.S. Pat. No. 5,374,522, it was believed by those skilled in the art that only with the inclusion of beads would the application of ultrasonic energy result in disruption of such difficult to lyse cells, such as mycobacterial cells.

A variety of ultrasonic baths are commercially available and useful for the present invention. Examples of suitable ultrasonic baths include those available from Branson Ultrasonics Corporation of Danbury, Connecticut which markets a number of models under the Bransonic® name with tank capacities ranging from 0.5 to 5.5 gallons, and operating frequencies around 42 +/−6% kHz. Mettler Electronics® of Anaheim, Calif. also markets several models with tank capacities ranging from 2.1 quarts to 18 gallons. Blue Wave Ultrasonics, Inc. of Davenport, Iowa markets a TT-0915 Table Top Cleaner with tank dimensions of 15.5"(l)×9"(w)× 6"(d), and an operating frequency around a baseline 30 kHz. LabLine Instruments, Inc. of Melrose Park, Ill. offers 28 Lab-Line® ultrasonic bath models with tank capacities ranging from 0.65 to 45 litres, including its model 9303 which operates at a fixed frequency of 35 kHz, features industrial type transducers, and has a temperature range from ambient to about 80° C. Also, VWRbrand Aquasonic Ultrasonic Cleaners offer ultrasonic cleaners with bath volume capacities ranging from 2.5 to 7.5 gallons, and operating frequencies of about 38.5 to about 40.5 kHz.

The Bransonic Ultrasonic Cleaner, Blue Wave Model TT-0915 and Aquasonic baths vary the ultrasonic frequency applied to the tank (i.e., sweeping frequency). The resultant effect of sweeping frequency is the substantial reduction or elimination of standing waves and hot spots found when only a fixed frequency bath is used. The Bransonic Model 2510 is particularly preferred for this sweeping frequency feature.

Such ultrasonic baths are recommended for cleaning tools, pens, jewelry, machinery, engine parts, nozzles, laboratory equipment, switches, locks, automobile parts, glass, ceramics, metals, hard plastics, etc. Ultrasonic cleaning baths such as these utilize a piezoelectric transducer such as, for example, lead zirconate titanate or barium titanate or a magnetorestrictive transducer to convert electrical input energy into high frequency ultrasonic energy. This mechanical energy, or vibration, is then coupled into and transmitted through the liquid contained in the cleaning tank.

The term ultrasonic refers to frequencies just above the range of human hearing, hence about 20 kHz. Alternatively, ultrasonic energy can be delivered directly to the solution or suspension of cells through, for example, a transducer. A solution or suspension of cells or microorganisms in purified or unpurified form can be placed in, for example, a vessel or well or a series of vessels or wells composed of a material capable of transmitting ultrasonic energy. The well is either attached to or is in proximity to a suitable transducer or other device capable of translating input energy into ultrasonic energy. The cells can be placed directly into the well or series of wells which act as sample holders, or, alternatively the cells can be placed in containers and submerged in liquid contained within the well. The well can be capped with a suitable closure to prevent leakage or aerosolization.

While the method by which ultrasound disrupts cells has not been fully elucidated, it is postulated that ultrasonic waves traveling through a liquid consist of alternate compressions and rarefactions. If the amplitude of the wave is high enough, a phenomenon known as cavitation is produced. Cavitation is the making and breaking of microscopic bubbles. As these bubbles or cavities grow to what is known as resonant size, they collapse instantly and violently in one compression cycle, producing high local pressure changes or perhaps 20,000 atmospheres. This mechanical shock, which is felt at a distance of a few microns, is responsible for cellular disruption in the case of the high power density instruments. (Alliger, H. *Ultrasonic Disruption*, reprinted from American Laboratory, October 1975.)

The cells which are subjected to ultrasonic energy in the ultrasonic bath may be any cells which are to be disrupted. More specifically, cells which contain nucleic acid for use in a subsequent molecular biology application, such as bacterial, viral, fungal and other nucleic acid containing cells can be subjected to the method of the present invention.

The cells will be in a second liquid, that is a liquid other than the liquid in the ultrasonic bath. Such second liquid may be the sample in which the cells are found or a liquid to which a cell sample is added. The second liquid containing the cells is held in a vessel such as a closed tube, and placed in the first liquid in the ultrasonic bath.

The cells of the organism to be lysed can be in $H_2O$, but also can be in suitable buffers such as Tris-buffered saline (50 mM Tris-HCl, pH8.0), phosphate-buffered saline (50 mM sodium phosphate, 150 mM NaCl, .pH8.0), polymerase chain reaction buffer (10 mM Tris-HCl, pH8.8, 50 mM KCl, 1.5 mM $MgCl_2$), React6 (buffer name React6 is registered by Bethesda Research Labs) (50 mM Tris-HCl, pH7.1, 50 mM NaCl, 50 mM KCl, 6 mM $MgCl_2$), sodium phosphate (pH 5.0 to 12.0), Trizma 9.0 (sigma; Trishydroxyaminomethylamine), and detergents such as 0.5% Tween 20 and 0.5% Nonidet P-40. The addition of detergents or any other agent which reduces surface tension of the liquid in which cells are suspended, or subjecting such liquid to any condition which reduces such surface tension, enhances the effects of the application of ultrasonic energy. A liquid of a lesser surface tension will cavitate more readily than a liquid of higher surface tension. Optionally, the heated sample can be centrifuged, making available the supernatant and pellet for subsequent use.

Although the application of ultrasonic energy to cells in the absence of beads was found to be effective in the present method for disruption of cells, the method may be enhanced by alkalinization of the second liquid in which the cells are located. More specifically, if the second liquid is rendered alkaline, the cell disruption method of the present invention is enhanced. Any suitable means for alkalinization of the second liquid can be used in the present invention. Examples of suitable alkalinization agents include KOH, NaOH, $Ca(OH)_2$, $Ba(OH)_2$, $NH_3$ and $Na_2CO_3$.

A further enhancement of the method of the present invention is the heating of the first (liquid in the ultrasonic bath. Maximum cavitation is known to occur in pure water at a temperature of approximately 71° C. as taught at the website for CAE Blackstone, 9 North Main Street, Jamestown, N.Y. 14701 (www.caeblackstone.com). Sufficient heat to enhance the disruption of cells with ultrasonic energy in the absence of beads is about 65° C. to about 75° C.

Heating of a sample may be accomplished by any suitable method. The heat range for disrupting the cells of a particular organism is readily obtainable by titrating different temperatures for different amounts of time against release of desired cellular components from the cells of an organism.

The heating will lyse the cells of the organism with subsequent release of intracellular components. One limitation on the heating is that the particular intracellular component of interest not be susceptible to destruction by the heat. Suitable heating means include water baths, microwave ovens, convection ovens, forced hot air ovens, and the like.

The heating time required for exposing intracellular components in the sample generally ranges from about two minutes to about forty-five minutes. The amount of heat and time of heat is readily found by sampling a portion of the cells of the organism to be lysed and examining for signs of lysis (e.g., detection of intracellular components), depending on the source from which the intracellular component is to be obtained.

The method of the present invention is most effective when the second liquid is of an alkaline pH, the first liquid is heated to about 65° C. to about 75° C. and the cells are subjected to ultrasonic energy ranging from about 35 kHz to about 45 kHz.

In the Examples below, the Applicants compared the method of the present invention to traditional methods for disrupting cells.

The following examples illustrate specific embodiments of the invention described in this document. As would be apparent to skilled artisans, various changes and modifications are possible and are contemplated within the scope of the invention described.

EXAMPLE 1

Comparison of Methods for Disrupting *Mycobacterium tuberculosis* Cells Using Sonication Without Beads vs. Physical Agitation with Beads The purpose of this Example was to determine if release of amplifiable nucleic acid from *M. tuberculosis* ("M. tb.") cells using a method employing ultrasonic treatment without beads is equivalent to release of amplifiable nucleic acid from M.tb cells using a method employing 5 m/sec physical agitation in the presence of zirconium beads. The comparison was based on amplification of a specific extracted nucleic acid target.

Materials
Sample Processing Reagents
22 Sputa: clinical samples
M.tb Negative NaLc pool
BBL Mycoprep NaLc-NaOH
BBL Mycoprep $PO_4$ Buffer
2 ml Labcraft sample processing tubes
Eppendorf micro centrifuge
Buffered GuSCN inhibitor removal wash
Sample Diluent
0.25N KOH
Tb Neutralization Solution
Zirconiurm beads encapsulated in onion skin glass
M.tb H37Rv -70° C. frozen stock DOM 110196
Lab-line® Ultrasonic Bath model 9303
Savant CellPrep Agitator
BD Lysolyser
Amplification and Assay Reagents
Oligonucleotide Devices (ODs)—microtiter plates with SDA amplification primers, SDA bumper primers, SDA fluorescence detector probes, dUTP and buffers dried in each well.
Enzyme Devices (ENDS)—microtiter plates with restriction endonuclease (BsoBI), polymerase (Bst), dCsTP, dATP, dGTP and buffers dried in each well (ODs and ENDs are more completely described in co-pending U.S. patent application Ser. No. 08/964,020 filed on Nov. 4, 1997, the disclosure of which is specifically incorporated herein by reference).

Procedure

Twenty-two sputa samples were processed to NaLc pellets by the procedure recommended by the CDC. Briefly, 5–10 mls of sputa was mixed with an equal volume of mucolytic decontaminating NaLc/NaOH, using BBL Mycoprep. The solution was allowed to stand for 15–20 minutes with occasional mixing. The solution was then neutralized with BBL Phosphate buffer to bring the final volume to 50 mls. The solution was then centrifuged at 3,000×g for 20 minutes. After decanting the supematant, 2 mls of phosphate buffer was used to resuspend the NaLc pellet.

Each NaLc sample was divided into two 500 μl aliquots and placed into each of two 2 ml sample processing tubes. All 500 μl aliquots were then spiked with enough M.tb H37Rv to represent 1.25 CFU in a final amplification reaction. A NaLc pool, previously validated as not containing M.tb, was included as a negative control. Samples were then processed by either of two nucleic acid extraction procedures.

In a first control procedure, samples were treated by a control condition involving physical agitation with zirconium beads. Briefly, 500 μl of NaLc sample was washed with 1 ml Buffered GuSCN inhibitor removal wash. After centrifugation at 12,200×g for 3 min., the supernatant was decanted. Three sample diluent washes followed. After decanting the supematant of the final wash, one 3 mm glass ball along with one capsule consisting of zirconium beads in onion skin glass was added to each tube. The tubes were then recapped and rendered non-infectious by heating in a forced air oven to 105 ° C. for 30 minutes in a BD Lysolyser. M.tb lysis proceeded by subjecting tubes to 5 m/sec physical agitation in the presence of zirconium beads in a Savant CellPrep Agitator. More detailed descriptions of the removal of inhibitors and the process for agitation with beads may be found in co-pending U.S. patent application Ser. No. 08/774,476 filed on Dec. 30, 1996, Ser. No. 08/614,230 filed on Mar. 12, 1996,. and Ser. No. 08/963,934 filed on Nov. 4, 1997, the disclosures of which are specifically incorporated herein by reference.

In the experimental condition, M.tb lysis occurred by subjecting the processed sample to high temperature, alkaline conditions, and ultrasonic energy. The 500 μl sample was washed, as in the control condition, with 1 ml Buffered GuSCN inhibitor removal wash. After centrifugation at 12,200×g for 3 min., the supematant was decanted. Three sample diluent washes followed. After decanting the supernatant of the final wash, 100 μl of 0.25N KOH was added. The recapped tubes were vortexed and then placed in a degassed Lab-line® Ultrasonic Bath model 9303. The bath temperature was 67 ° C. at the start of fixed frequency 35 kHz treatment. Following 30 minutes sonication, the bath temperature was 75° C. A 600 μl volume of Tb Neutralization Solution was then added and the recapped tubes were vortexed. The samples were then rendered non-infectious after being placed in a forced air oven to 105 ° C. for 30 minutes in a BD Lysolyser. Spiked samples were then amplified and assayed in duplicate. The negative control was run as a single replicate.

Aliquots (~150 μl) of a sample from the tubes treated by both M.tb lysis procedures, were dispensed into each well of the ODs. The wells of the ODs were covered, and the ODs retained at room temperature for 20 minutes. The ODs were then uncovered, and incubated at 75° C. for 10 minutes, while the ENDs were pre-warmed for 10 minutes to 52° C.

After the 10 minute incubation, 100 µl aliquots from each well of the ODs were transferred (pipetted) to a corresponding well in the ENDs. The ENDs were then sealed with an adhesive cover, and introduced into a fluorescence reader instrument as described in co-pending U.S. patent application Ser. No. 08/929,895 filed Sep. 15, 1997, the disclosure of which is specifically incorporated herein by reference.

The fluorescence signal from the wells of the ENDs were monitored for 60 minutes. MOTA units, derived from the integration of the fluorescent signal curve over time, were used for determining positive and negative M.tb nucleic acid amplification. The results are shown below.

RESULTS

| Sputum ID | M.tb Spiked 1.25 CFU/rxn | M.tb Lysis by Using Agitation with Beads MOTA | M.tb Lysis by Using Sonication Without Beads MOTA |
|---|---|---|---|
| 551 | + | 2323 | 4487 |
|  |  | 801 | 4186 |
| 2879 | + | 53709 | 309 |
|  |  | 50886 | 248 |
| 2170 | + | 1966 | 2298 |
|  |  | 2606 | 2061 |
| 66 | + | 1440 | 27014 |
|  |  | 232 | 8279 |
| 2194 | + | 4120 | 19688 |
|  |  | 249 | 9164 |
| 2895 | + | 47602 | 21728 |
|  |  | 14301 | 3814 |
| 2075 | + | 4354 | 35329 |
|  |  | 2412 | 36942 |
| 83 | + | 37455 | 30893 |
|  |  | 53158 | 29242 |
| 2990 | + | 29129 | 31034 |
|  |  | 8699 | 37232 |
| 78 | + | 4434 | 118 |
|  |  | 1112 | 1260 |
| 877 | + | 17257 | 31416 |
|  |  | 3940 | 30390 |
| 7 Subpool | − | 251 | 357 |
| 3140 | + | 13754 | 46556 |
|  |  | 32867 | 42993 |
| 3316 | + | 45048 | 6223 |
|  |  | 39390 | 6420 |
| 3593 | + | 1010 | 518 |
|  |  | 326 | 2293 |
| 3614 | + | 202 | 1369 |
|  |  | 253 | 1464 |
| H36198 | + | 4574 | 23657 |
|  |  | 4258 | 16531 |
| M9287 | + | 20170 | 8836 |
|  |  | 2988 | 7597 |
| F45663 | + | 14379 | 2993 |
|  |  | 20878 | 977 |
| SF 1300 | + | 1275 | 901 |
|  |  | 699 | 538 |
| 1338 | + | 21540 | 2422 |
|  |  | 3902 | 1535 |
| 1360 | + | 4679 | 20601 |
|  |  | 5244 | 25445 |
| 1389 | + | 3045 | 276 |
|  |  | 2212 | 320 |
| 7 Subpool | − | 358 | 300 |
| MEAN |  | 13293 | 13355 |
| S.D. |  | 16852 | 14311 |

For each experimental set of 11 samples, the data was statistically analyzed through a randomized complete block design with subsampling model. ROC analysis was used to calculate the sensitivity rates for the two sample processing procedures. Lastly, distributions were compared by empirical comparison through the Kolmogorov-Smirnov test.

There were no significant differences seen between the means of the two sample processing procedures in either experimental set. From the ROC analysis, sensitivity curves appeared to be equivalent for the two procedures. The distributions of MOTA generated by the two procedures appear to be identical (p-value of first experimental set 0.6208 and 0.8603 of second experimental set).

Conclusion

No apparent differences in the effectiveness of M.tb lysis procedures exists between a control method employing agitation with zirconium beads and a novel method employing ultrasonic treatment without beads. The control method has been shown to provide greater than 90% sensitivity of acid fast bacilli (AFB) smear negative, culture positive M.tb clinical samples as evidenced by: (1) G. E. Pfyffer et. al., Study for the direct detection of M. tb complex in respiratory specimens presented at ICAAC 1997 abstract D92 (91.7% AFB smear negative sensitivity); (2) G. Woods et al., who analyzed respiratory specimens and found a resolved sensitivity of 100% for AFB smear negative M. tb clinical samples (American Society for Microbiology 98th General Meeting abstract C-301); and (3) an evaluation of AFB smear negative, culture positive M. tb freshly processed NaLc which resulted in sensitivity of 92% (T. Fort et al Presented at Clinical Microbiology and Infection, 8th Meeting, vol.3, supplement 2, May 1997 abstract P677).

EXAMPLE 2

Optimization of Novel Cell Lysis Method Employing Sonication Without Beads

The purpose of this experiment was to optimize the conditions for the novel cell lysis method employing ultrasonic treatment without beads. Temperature was varied from ambient to the previously tested 67–75° C. Alkaline conditions were varied from neutral pH 7.25 to alkaline pH 13.6. Duration of ultrasonic treatment varied from no treatment to 30 minutes. Face-centered experimental design was utilized to determine significant and optimal conditions.

Materials

Sample Processing Reagents

BBL Mycoprep $PO_4$ Buffer 2 ml Labcraft sample processing tubes

Eppendorf micro centrifuge 0.25N KOH, pH 13.6

0.000416N KOH, pH 10.46 deionized $H_2O$, pH 7.25 pH 7.99, Tb Neutralization Solution pH 8.69, Tb Neutralization Solution

M.tb H37Rv −70° C. frozen stock DOM 040798

Lab-line® Ultrasonic Bath model 9303

BD Lysolyser

Amplification and Assay Reagents

As listed in Example 1

Procedure

Ninety 2 ml sample processing tubes were numbered 1–90. One ml of BBL Mycoprep $PO_4$ Buffer was aliquotted to each tube. Each tube was then spiked with a volume of M.tb H37Rv to give a final concentration of 1.5 CFU per amplification reaction. All tubes were then microfuged at 12,200×g for 3 min. and the supernatant was decanted. All tubes were rendered non-infectious in a BD Lysolyser for 30 min. at 105 ° C.

Tubes numbered 66–90 were resuspended with 100 µl of the appropriate KOH solution as determined by the experimental design found in the results section. The tubes were then placed in a degassed, 67.5 ° C. prewarmed Lab-line® Ultrasonic Bath model 9303 and sonicated for the time determined by the experimental design.

Tubes numbered 26–65 were resuspended with 100 µl of the appropriate KOH solution as determined by the experimental design found in the results section. The tubes were then placed in a degassed, 41.9° C. prewarmed Lab-line® Ultrasonic Bath model 9303 and sonicated for the time determined by the experimental design.

Tubes numbered 1–25 were resuspended with 100 µl of the appropriate KOH solution as determined by the experimental design found in the results section. The tubes were then placed in a degassed, 23.1° C. ambient Lab-line® Ultrasonic Bath model 9303 and sonicated for the time determined by the experimental design.

Immediately following ultrasonic treatment, 600 µl of Tb Neutralization Solution was added to each tube to bring the final pH of the amplification reaction to pH 8.69. For pH 13.6/250 mM KOH treated samples, pH 7.99 Tb Neutralization Solution was used. pH 8.69 Tb Neutralization Solution was used for all other tubes. After vortexing the samples, the reaction volumes were amplified and assayed for specific M.tb target nucleic acid as in Example 1. The results are shown below.

RESULTS

| Tube Number | Target Temperature ° C. | pH/[KOH] | Duration (min.) | MOTA (mean of 5 replicates) |
|---|---|---|---|---|
| 1–5 | 19–30 | 7.25/none | 0 | 6013 |
| 6–10 | 19–30 | 7.25/none | 30 | 11148 |
| 11–15 | 19–30 | 10.46/416 µM | 15 | 32662 |
| 16–20 | 19–30 | 13.60/250 mM | 0 | 20153 |
| 21–25 | 19–30 | 13.60/250 mM | 30 | 55027 |
| 26–30 | 44–45 | 7.25/none | 15 | 27788 |
| 31–35 | 44–45 | 10.46/416 µM | 0 | 12100 |
| 36–40 | 44–45 | 10.46/416 µM | 15 | 39772 |
| 41–45 | 44–45 | 10.46/416 µM | 15 | 15693 |
| 46–50 | 44–45 | 10.46/416 µM | 15 | 41613 |
| 51–55 | 44–45 | 10.46/416 µM | 15 | 24301 |
| 56–60 | 44–45 | 10.46/416 µM | 30 | 41073 |
| 61–65 | 44–45 | 13.60/250 mM | 15 | 54081 |
| 66–70 | 69–80 | 7.25/none | 0 | 14852 |
| 71–75 | 69–80 | 7.25/none | 30 | 12089 |
| 76–80 | 69–80 | 10.46/416 µM | 15 | 18544 |
| 81–85 | 69–80 | 13.60/250 mM | 0 | 30508 |
| 86–90 | 69–80 | 13.60/250 mM | 30 | 53863 |

Statistical analysis to determine significant factors found that a t-value of 4.763 (significance cutoff=0.05) was found for pH with increasing pH optimal for M.tb lysis. Duration of ultrasonic treatment was also significant with a t-value of 3.01. Increasing duration of ultrasonic treatment to 30 minutes was found to be optimal with a plateau effect within the 15–30 minute timeframe. Response surface plots generated from the experiment presented in FIG. 1 show the combinatorial effect of increasing pH and duration of sonication. The R-squared value of the experimental response was 0.838.

Conclusion

The optimal factors for the lysis of M.tb have been found to be extreme alkaline conditions, for 30 minutes, when 35 kHz of ultrasonic treatment is used. The use of alkali conditions may alter the conformation of proteins found in cell membranes, thus facilitating the extraction of nucleic acid, when used in conjunction with ultrasonic energy. Using a frozen stock of M.tb H37Rv, temperature was found to be insignificant.

EXAMPLE 3

Confirmation of Temperature Requirements for Alkali Sonication Without Beads

The purpose of this experiment was to confirm temperature requirements for the lysis of freshly prepared M.tb H37Rv cells. The previous examples have employed a frozen stock of M.tb H37Rv and have determined that heating of an ultrasonic bath is unnecessary for the effective lysis of M.tb.

Materials

Sample Processing Reagents
BBL Mycoprep $PO_4$ Buffer
2 ml Labcraft sample processing tubes
Eppendorf micro centrifige
0.25N KOH, pH 13.6
pH 7.99, Tb Neutralization Solution
Freshly prepared M.tb H37Rv
Lab-line® Ultrasonic Bath model 9303
BD Lysolyser
Amplification and Assay Reagents
As listed in Example 1

Procedure

BBL Phosphate Buffer was pipetted into 26 tubes, 1 ml volume for each tube. Eight tubes were spiked with an appropriate volume such that 1.07 particles of freshly prepared M.tb H37Rv were present in an amplification reaction. The addition of freshly prepared M.tb was repeated in separate tubes at 0.71 and 0.38 particles/rxn. Two tubes were left unspiked with M.tb as a sample processing control.

All tubes were then centrifuged at 12,200×g for 3 min. and the supernatant was decanted. M.tb was rendered noninfectious by subjecting the tubes to 105° C. for 30 minutes in a BD Lysolyser.

One half of the tubes, at each concentration of M.tb spiked, was resuspended with 100µl of 0.25N KOH and vortexed. The tubes were then placed in a degassed, 63.0° C. prewarned Lab-line® Ultrasonic Bath model 9303 and sonicated for 30 minutes.

The remaining tubes, at each concentration of M.tb spiked was resuspended with 100 µl of 0.25N KOH and vortexed. The tubes were then placed in a degassed, 25.2° C. prewarmed Lab-line® Ultrasonic Bath model 9303 and sonicated for 30 minutes.

All tubes were neutralized immediately following ultrasonic treatment with 600 µl pH 7.99 Tb Neutralization solution and vortexed. The reaction volumes were amplified in triplicate and assayed for specific M.tb target nucleic acid as in Example 1. Freshly prepared M.tb H37Rv was plated for colony count quantification. The results are shown below.

RESULTS

| | Lysis Temp. 63.0–73.6° C. TB MOTA | Lysis Temp. 25.2–32.9° C. TB MOTA |
|---|---|---|
| M.tb 1.90 CFU/ml | | |
| N = | 12 | 12 |
| Mean | 33683 | 19996 |
| Stdev | 26465 | 23288 |
| C.V. | 72 | 117 |
| M.tb 1.28 CFU/ml | | |
| N = | 12 | 12 |
| Mean | 33764 | 18171 |
| Stdev | 22794 | 13062 |
| C.V. | 68 | 72 |
| M.tb 0.70 | | |

-continued

| | RESULTS | |
|---|---|---|
| | Lysis Temp. 63.0–73.6° C. TB MOTA | Lysis Temp. 25.2–32.9° C. TB MOTA |
| CFU/ml | | |
| N = | 12 | 12 |
| Mean | 19646 | 9707 |
| Stdev | 22131 | 11128 |
| C.V. | 113 | 115 |
| M.tb 0 CFU/ml | | |
| N = | 3 | 3 |
| Mean | 993 | 844 |
| Stdev | 13515 | 9230 |
| C.V. | 1362 | 1094